US00PP26583P2

(12) United States Plant Patent
Renault

(10) Patent No.: US PP26,583 P2
(45) Date of Patent: Apr. 5, 2016

(54) ***HYDRANGEA* PLANT NAMED 'RENCRI'**

(50) Latin Name: *Hydrangea paniculata*
Varietal Denomination: RENCRI

(71) Applicant: Jean Renault, Gorron (FR)

(72) Inventor: Jean Renault, Gorron (FR)

( * ) Notice: Subject to any disclaimer, the term of this patent is extended or adjusted under 35 U.S.C. 154(b) by 20 days.

(21) Appl. No.: 14/121,328

(22) Filed: Aug. 20, 2014

Related U.S. Application Data

(60) Provisional application No. 61/959,962, filed on Sep. 5, 2013.

(51) Int. Cl.
*A01H 5/02* (2006.01)

(52) U.S. Cl.
USPC ..... Plt./250

(58) Field of Classification Search
USPC ..... Plt./250
CPC ..... A01H 5/02; A01H 5/00
See application file for complete search history.

(56) References Cited

PUBLICATIONS http://www.sapho.fr/gb/trees-and-shrubs/153-hydrangea-paniculata-dentelle-de-gorron-rencri.html; 2013; 6 pages.*

* cited by examiner

*Primary Examiner* — Kent L Bell
(74) *Attorney, Agent, or Firm* — Penny J. Aguirre

(57) ABSTRACT

A new cultivar of *Hydrangea paniculata*, 'RENCRI', that is characterized by its large panicles of sterile and fertile flowers that are white in color with the terminal portion of the panicle light green, its airy panicles due to having sterile flowers with thin and long sepals on long pedicels, its very early blooming habit, and its open mounded well branched plant habit.

2 Drawing Sheets

Genus/species: *Hydrangea paniculata.*
Varietal denomination: 'RENCRI'.

BACKGROUND OF THE INVENTION

The present invention relates to a new and distinct cultivar of *Hydrangea paniculata* and will be referred to hereafter by its cultivar name, 'RENCRI'. 'RENCRI' represents a new deciduous shrub grown for landscape use.

The new *Hydrangea* resulted from a controlled breeding program conducted by the Inventor in Gorron, France. The Inventor made crosses in 1998 between unnamed proprietary plants of *Hydrangea paniculata* in the Inventor's breeding program as both the female parent and male parent. The exact characteristics of the parents are unknown as seeds were pooled and sown from several crosses. 'RENCRI' was selected as a single unique plant in 2005 from the resulting seedlings of the above crosses.

Asexual propagation of the new cultivar was first accomplished by softwood cuttings in 2005 by the inventor in Mayenne, France. Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish in 'RENCRI' as a unique cultivar of *Hydrangea paniculata.*

1. 'RENCRI' exhibits large panicles of sterile and fertile flowers that are white in color with the terminal portion of the panicle light green.

2. 'RENCRI' exhibits airy panicles due to having sterile flowers with thin and long sepals on long pedicels.
3. 'RENCRI' exhibits a very early blooming habit.
4. 'RENCRI' exhibits an open mounded plant habit and is well branched.

'RENCRI' can be compared to the cultivars 'Midlate Summer' (not patented) and 'Brussel's Lace' (not patented). 'Midlate Summer' is similar to 'RENCRI' in having panicles of white sterile and fertile flowers. 'Midlate Summer' differs from 'RENCRI' in having a later bloom season and in having smaller panicles that are not green at the terminal end and have sterile flowers. 'Brussel's Lace' is similar to 'RENCRI' in having panicles of white sterile and fertile flowers and in having sterile flowers that are similar in size. 'Brussel's Lace' differs from 'RENCRI' in having a later bloom season and in having panicles that are not green at the terminal end and have less sterile flowers.

BRIEF DESCRIPTION OF THE DRAWINGS

The drawings presented are digital photographs taken of plants 5 years in age as grown in a garden in Gorron, France.

Figure 1:
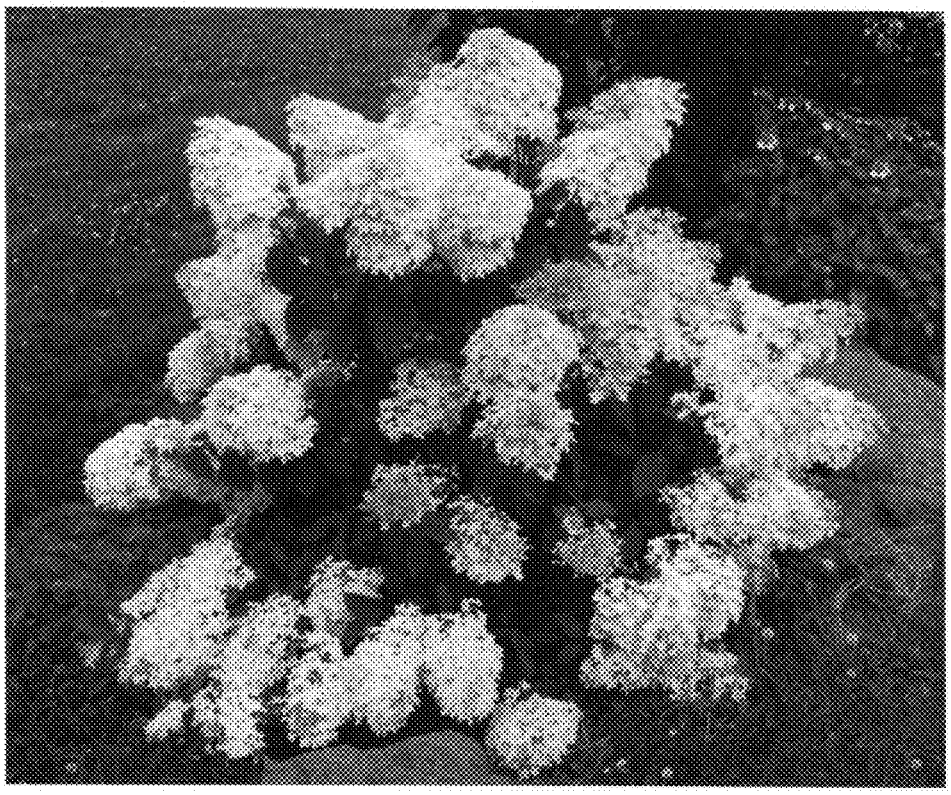
FIG. 1 provides a view of the plant habit and flowering habit of 'RENCRI'.
Figure 2:
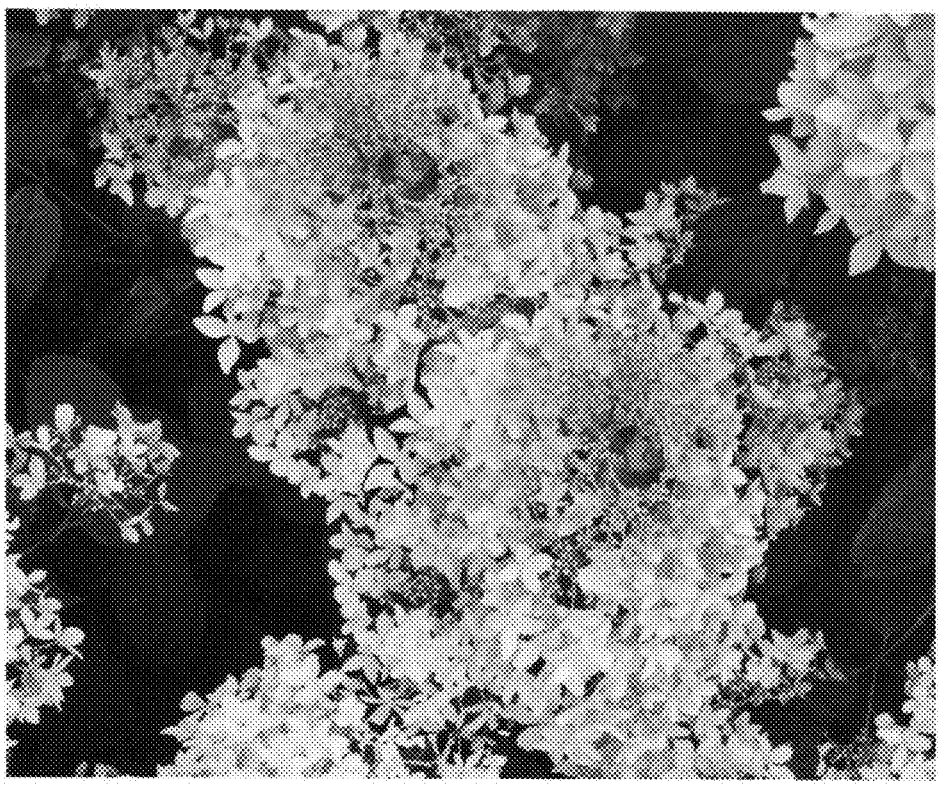
FIG. 2 provides a close-up view of the inflorescences of 'RENCRI'.

The colors in the photographs are as close as possible with the photographic and printing technology utilized and color values cited in the detailed botanical description accurately describe the colors of the new *Hydrangea.*

BOTANICAL DESCRIPTION OF THE PLANT

The following is a detailed description of the new cultivar as observed on 5 year-old plants of the new cultivar as grown outdoors in a trial garden in Gorron, France. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period*.—From early June to mid September in western France.

*Plant habit*.—Open mounded.

*Height and spread*.—Reaches 2 to 2.5 m in height and 2 m width.

*Cold hardiness*.—At least in U.S.D.A. Zone 4.

*Diseases and pests*.—No susceptibility or resistance to diseases or pests has been observed.

*Root description*.—Fibrous.

*Propagation*.—Softwood stem cuttings.

*Growth rate*.—Moderately vigorous.

Stem description:

*Shape shape*.—Round, solid.

*Stem color*.—New wood 146D, mature wood N199D, old wood (dormant); N200B to N200C.

*Stem diameter*.—Average of 6 mm.

*Stem surface*.—Pubescent when young becoming glabrous.

*Internode length*.—Average of 8 cm.

*Branching*.—A single dormant stem will produce an average of 5 primary branches. Subsequent branching is determined by pinching; 2 stems develop per pinched node.

Foliage description:

*Leaf shape*.—Elliptic.

*Leaf division*.—Simple.

*Leaf base*.—Cuneate.

*Leaf apex*.—Primarily acuminate.

*Leaf venation*.—Pinnate, recessed, color 145C on upper surface and 145D on lower surface.

*Leaf margins*.—Serrated.

*Leaf attachment*.—Petiolate.

*Leaf arrangement*.—Opposite.

*Leaf surface*.—Glabrous on upper and lower surface.

*Leaf color*.—Newly formed leaves upper surface; 144A, newly formed leaves lower surface; 146D, mature leaves upper surface; 137B to 137C, mature leaves lower surface; 138B to 138C.

*Petioles*.—Average of 2 cm in length and 2 mm in width, sulcate in shape, stipules absent, 145C to 145D in color.

Flower description:

*Inflorescence type*.—Light and airy pyramidal-shaped panicles of sterile flowers and fertile flowers.

*Lastingness of inflorescence*.—Persistent but color is retained for 4 to 6 weeks before browning.

*Inflorescence size*.—12 to 15 cm in diameter and 15 to 20 cm in length.

*Inflorescence number*.—One per stem, new shoots develop throughout the summer.

*Flower number*.—Numerous, approximately 250 sterile flowers and 1500 fertile flowers per inflorescence.

*Fragrance*.—None.

*Flower size*.—Sterile flowers; average of 2.5 cm in diameter and 8 mm in depth, fertile flowers; average of 5 mm in diameter and 4 mm in depth.

*Flower buds*.—Sterile flowers: globose in shape, up to 2 mm in length and 1 mm in width, 155B in color, fertile flowers; globose in shape, up to 4 mm in length and 2 mm in width, NN155A in color.

*Peduncles*.—Average of 5 cm in length and 2 mm in width, 160B in color, surface moderately covered with minute pubescence, held between the angles of 60° and 80°.

*Pedicels*.—Sterile flowers; moderate strength, an average of 2 cm in length and 1 mm in width, 155C in color, surface is moderately covered with very short soft pubescence matching pedicel color, average hair size is 0.5 mm in length, held between the angles of 60° and 80°, fertile flowers; and average of 3 mm in length and 0.5 mm in width, moderate in strength, texture is smooth and dull.

*Fertile flowers*.—Rotate in shape, lasting about 7 days on the plant, not persistent on the plant (self cleaning), petals; 5, 155C in color changing to 194C in color on both surfaces, about glabrous on both surfaces, average of 2.5 mm in length and 0.5 mm in width, sepals; 5 fused in campanulate calyx, average of 1.5 mm in width, NN155A in color and glabrous on both surfaces.

*Sepals* (*sterile flowers*).—4 to 5, un-fused, not overlapping, rotate in arrangement, smooth, dull and glabrous on both surfaces, broadly elliptic to broadly ovate in shape, held slightly upwards when fully open, entire margin, apex is rounded to broadly acute, average of 1.5 cm in length and 1 cm in width, color of upper and lower surfaces when newly open at the end of summer is 155C, color of upper and lower surfaces when mature in mid summer NN155A, color when mature in late summer upper surface 149D, color when mature in late summer lower surface 149D.

*Eye of sterile flowers* (*petal spot*).—3 mm in diameter, 2 mm in depth, NN155A in color.

Reproductive organs (fertile flowers):

*Stamens*.—Average of 10, anther is 1 mm in length and NN155A in color, filament is an average of 3 mm in length and NN155C in color, pollen is low in quantity and 160C in color.

*Pistils*.—Average of 3, average of 5 mm in length and 145B in color, style is an average of 3 mm in length and 145B in color, stigma is club shaped and 145B in color (newly opened blooms).

*Fruit and seed*.—None observed.

It is claimed:

1. A new and distinct cultivar of *Hydrangea* plant named 'RENCRI' as herein illustrated and described.

* * * * *